U
United States Patent [19]

Koppel et al.

[11] 4,038,275

[45] July 26, 1977

[54] PROCESS FOR PREPARATION OF 3-HYDROXYMETHYLCEPHEMS

[75] Inventors: Gary A. Koppel, Indianapolis, Ind.; Laurence J. Nummy, Cambridge, Mass.

[73] Assignee: Eli Lilly and Company, Indianapolis, Ind.

[21] Appl. No.: 678,086

[22] Filed: Apr. 19, 1976

[51] Int. Cl.² ........................................... C07D 501/04
[52] U.S. Cl. ............................... 260/243 C; 424/246
[58] Field of Search ...................................... 260/243 C

[56] References Cited

U.S. PATENT DOCUMENTS

| 3,948,906 | 4/1976 | Eardley et al. | 260/243 C |
| 3,950,329 | 4/1976 | Boswell et al. | 260/243 C |

Primary Examiner—Nicholas S. Rizzo
Attorney, Agent, or Firm—Steven R. Lammert; Everet F. Smith

[57] ABSTRACT

3-Hydroxymethyl-2-cephems are provided by (1) reacting a 2-halomethylcephem compound with a γ-hydroxycarboxylic acid salt or a δ-hydroxycarboxylic acid salt and (2) reacting the novel γ or δ-hydroxy esters thereby obtained with a protic acid. The 3-hydroxymethylcephems provided by the process of this invention are useful intermediates for the preparation of known cephalosporin antibiotics.

9 Claims, No Drawings

PROCESS FOR PREPARATION OF 3-HYDROXYMETHYLCEPHEMS

BACKGROUND OF THE INVENTION

This invention relates to the cephalosporin class of antibiotics. In particular, this invention relates to a process for preparing 3-hydroxymethyl-2-cephem compounds and to certain cephem ester intermediates therein.

3-Hydroxymethylcephems are known in the cephalosporin art and have proved to be useful intermediates for the preparation of many related cephalosporin antibiotic compounds. Heretofore 3-hydroxymethylcephems have been generally available by chemical or enzymatic deesterification procedures from the corresponding 3-acetoxymethylcephems (derivatives of cephalosporin C). Thus a 7-acylamino-3-acetoxymethyl-3-cephem-4-carboxylic acid can be treated with an esterase derived from *Bacillus subtilis* or with orange peel esterase to form the corresponding 7-acylamino-3-hydroxymethyl-3-cephem-4-carboxylic acid. The preparation and recognized utility of 3-hydroxymethylcephems, products of the process of the present invention, has been disclosed generally in U.S. Pat. Nos. 3,196,151, issued July 20, 1965; 3,218,318, issued Nov. 16, 1965; 3,436,310, issued Apr. 1, 1969; and 3,459,746, issued Aug. 5, 1969.

SUMMARY OF THE INVENTION

This invention is directed to a process for preparing 3-hydroxymethyl-2-cephem compounds by (1) reacting a 3-halomethyl-2-cephem or 3-halomethyl-3-cephem with an alkali metal salt of a γ or δ-hydroxycarboxylic acid in hexamethylphosphoramide and (2) reacting the product 2-cephem esters with a protic acid.

A further embodiment of the present invention provides cephem compounds of the formula

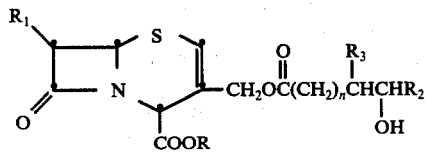

wherein R is a carboxylic acid protecting group; $R_1$ is acylamino; $R_2$ and $R_3$ are independently hydrogen, methyl or ethyl; and n is 1 or 2. Such compounds are useful as intermediates in the process of the present invention, that is, the conversion of 3-halomethylcephems to 3-hydroxymethylcephems.

DETAILED DESCRIPTION OF THE INVENTION

This invention provides a process for preparing a 3-hydroxymethyl-2-cephem compound of the formula

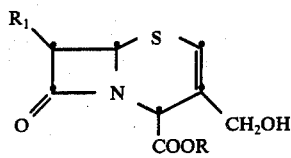

which comprises 1. reacting a 3-halomethylcephem compound of the formula

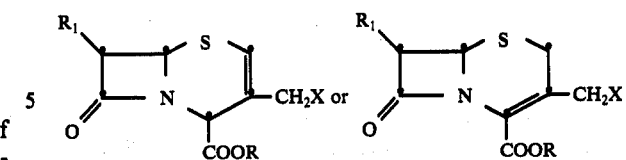

with from about 1 to about 1.3 equivalents of a salt of a γ-hydroxycarboxylic acid of the formula

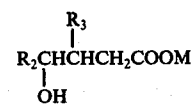

or a salt of a δ-hydroxycarboxylic acid of the formula

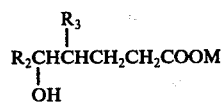

in hexamethylphosphoramide (HMPA) at a temperature of about −10° to about 25° C. to provide a mixture of the 2-cephem hydroxy ester of the formula

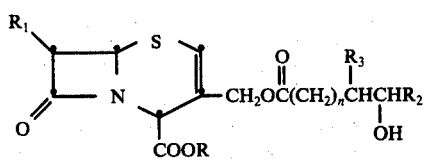

and the corresponding 3-cephem hydroxy ester; and 2. reacting in an inert organic solvent the product 2-cephem hydroxy ester with a protic acid having a pK value of less than about 4.0; wherein in the above formulae X is chloro, bromo, or iodo;
M is an alkali metal cation;
n is 1 or 2;
R is a carboxylic acid protecting group;
$R_2$ and $R_3$ are independently hydrogen, ethyl or methyl; and
$R_1$ is an amido group of the formula

wherein $R_4$ is
a. hydrogen, $C_1$–$C_3$ alkyl, 3-(2-chlorophenyl)-5-methylisoxazol-4-yl or 4-protected amino-4-protected carboxybutyl;
b. benzyloxy, 4-nitrobenzyloxy, 2,2,2-trichloroethoxy, tert-butoxy, or 4-methoxybenzyloxy;
c. the group —R" wherein R" is 1,4-cyclohexadienyl, phenyl or phenyl substituted with 1 or 2 substituents independently selected from the group consisting of halo, protected hydroxy, nitro, cyano, trifluoromethyl, $C_1$–$C_3$ alkyl, and $C_1$–$C_7$ alkoxy;
d. an arylalkyl group of the formula

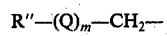

wherein R" is as defined above, Q is O or S, and m is 0 or 1;
e. a substituted arylalkyl group of the formula

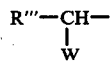

wherein R''' is R'' as defined above, 2-thienyl or 3-thienyl, and W is protected hydroxy, protected carboxy or protected amino; or f. a heteroarylmethyl group of the formula

wherein R'''' is 2-thienyl, 3-thienyl, 2-furyl, 2-thiazolyl, 5-tetrazolyl, and 1-tetrazolyl.

The present invention is also directed to the aforementioned intermediate cephem esters of the formula

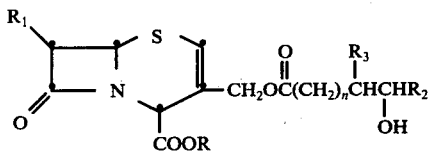

wherein R, $R_1$, $R_2$ and $R_3$ are as defined hereinabove.

In the foregoing definition of the present invention the term "$C_1$-$C_3$ alkyl" refers to methyl, ethyl, n-propyl or isopropyl. The term "halomethyl" refers to chloromethyl, bromomethyl, or iodomethyl. Exemplary of "$C_1$-$C_7$ alkoxy" groups are methoxy, ethoxy, propoxy, n-butoxy, tert-butoxy, cyclohexyloxy and like groups.

When in the above definition R'' represents a substituted phenyl group, R'' can be a mono or disubstituted halophenyl group such as 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a protected hydroxy phenyl group such as 4-benzyloxyphenyl, 3-benzyloxyphenyl, 4-tert-butoxyphenyl, 4-tetrahydropyranyloxyphenyl, 4-(4-nitrobenzyloxy)phenyl, 2-phenacyloxyphenyl, 4-benzhydryloxyphenyl, 4-trityloxyphenyl and like groups; a nitrophenyl group such as 3-nitrophenyl or 4-nitrophenyl; a cyanophenyl group, for example, 4-cyanophenyl; a mono or dialkyl substituted phenyl group such as 4-methylphenyl, 2,4-dimethylphenyl, 2-ethylphenyl, 4-isopropylphenyl, 4-ethylphenyl, 3-n-propylphenyl and the like; a mono or dialkoxyphenyl group, for example, 2,6-dimethoxyphenyl, 4-methoxyphenyl, 3-ethoxyphenyl, 4-isopropoxyphenyl, 4-tert-butoxyphenyl, 3-ethoxy-4-methoxyphenyl and the like. Also, R'' represents disubstituted phenyl groups wherein the substituents can be different for example, 3-methyl-4-methoxyphenyl, 3-chloro-4-benzyloxyphenyl, 2-methoxy-4-bromophenyl, 4-ethyl-2-methoxyphenyl, 3-chloro-4-nitrophenyl, 2-methyl-4-chlorophenyl and like disubstituted phenyl groups bearing different substituents.

The term "protected amino" as employed in the above definition has reference to an amino group substituted with one of the commonly employed amino blocking groups such as the tert-butoxycarbonyl group (t-BOC); the benzyloxycarbonyl group, the 4-methoxybenzyloxycarbonyl group, the 4-nitrobenzyloxycarbonyl group, or the 2,2,2-trichloroethoxycarbonyl group. Like conventional amino protecting groups such as those described by J. W. Barton in "Protective Groups in Organic Chemistry," J. F. W. McOmie, Ed., Plenum Press, New York, N.Y., 1973, Chapter 2 shall be recognized as suitable.

The term "protected hydroxy" has reference to the readily cleavable groups formed with an hydroxyl group such as the formyloxy group, the chloroacetoxy group, the benzyloxy group, the benzhydryloxy group, the trityloxy group, the 4-nitrobenzyloxy group, the trimethylsilyloxy group, the phenacyloxy group, the tert-butoxy group, the methoxymethoxy group, the tetrahydropyranyloxy group, and the like. Other hydroxy protecting groups, including those described by C. B. Reese in "Protective Groups in Organic Chemistry", supra, Chapter 3 shall be considered as within the term "protected hydroxy" as used herein.

The term "protected carboxy" has reference to a carboxy group which has been protected by one of the commonly used carboxylic acid protecting groups employed to block or protect the carboxylic acid functionality while reactions involving other functional sites of the compound are carried out. Such protected carboxy groups are noted for their ease of cleavage by hydrolytic or by hydrogenolytic methods to the corresponding carboxylic acid. Examples of carboxylic acid ester protecting groups include tert-butyl, benzyl, 4-methoxybenzyl, $C_2$-$C_6$ alkanoyloxymethyl, 4-nitrobenzyl, diphenylmethyl (benzhydryl), phenacyl, p-halophenacyl, 2,2,2-trichloroethyl, succinimidomethyl, tri-($C_1$-$C_3$ alkyl)silyl and like ester forming moieties. Other known conventional carboxy protecting groups such as those described by E. Haslam in "Protective Groups in Organic Chemistry", supra, Chapter 5, shall be recognized as suitable. The nature of such ester forming groups is not critical so long as the particular ester formed therewith is stable under the reaction conditions described hereinafter. Preferred carboxylic acid ester protecting groups are tert-butyl, 4-methoxybenzyl, benzhydryl, 4-nitrobenzyl, and 2,2,2-trichloroethyl; most preferred are 4-nitrobenzyl and 2,2,2-trichloroethyl.

In the foregoing definitions, hydroxy, amino, and carboxy protecting groups are not exhaustively defined. The function of such groups is to protect the reactive functional groups during the preparation of the desired products and then be removed without disrupting the remainder of the molecule. Many such protective groups are well known in the art and the use of other groups equally applicable to the process and compounds of the present invention shall be recognized as suitable. Thus, there is no novelty or inventiveness asserted with regard to the "protecting groups" alluded to in this specification, nor is it intended that the invention be limited by the groups specifically disclosed herein.

Likewise the nature of the side chain group $R_1$ is not critical to the process of this invention. Under the relatively mild reaction conditions the amide side chain moiety remains unaffected. The process of this invention is therefore applicable to a wide variety of 7-acylamino-3-halomethylcephem starting materials, the source of which is detailed hereinbelow.

Representative of the acylamino group,

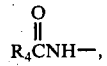

as defined hereinabove are formamido, acetamido, propionamido, butyramido, 2-pentenoylamino, 5-tertbutoxycarbonylamino-5-tert-butoxycarbonyl-valeramido, and the like.

Illustrative of the particular acylamino group,

are benzamido, 2,6-dimethoxybenzamido, 4-chlorobenzamido, 4-methylbenzamido, 3,4-dichlorobenzamido, 4-cyanobenzamido, 3-bromobenzamido, 3-nitrobenzamido and the like.

Exemplary of the acylamino group

when $R_4$ is a group of the formula $R''(Q)_mCH_2—$ and $m$ is 0, are cyclohexa-1,4-dienylacetamido, phenylacetamido, 4-chlorophenylacetamido, 3-methoxyphenylacetamido, 3-cyanophenylacetamido, 3-methylphenylacetamido, 4-bromophenylacetamido, 4-ethoxyphenylacetamido, 4-nitrophenylacetamido, 3,4-dimethoxyphenylacetamido and the like; and when $m$ is 1 and Q is O, representative acylamino groups are phenoxyacetamido, 4-cyanophenoxyacetamido, 4-chlorophenoxyacetamido, 3,4-dichlorophenoxyacetamido, 2-chlorophenoxyacetamido, 4-methoxyphenoxyacetamido, 2-ethoxyphenoxyacetamido, 3,4-dimethylphenoxyacetamido, 4-isopropylphenoxyacetamido and like substituted phenoxyacetamido groups; and when $m$ is 1 and Q is S representative acylamino groups are phenylthioacetamido, 2,5-dichlorophenylthioacetamido, 4-bromophenylthioacetamido, 4-methoxyphenylthioacetamido, 3-nitrophenylthioacetamido, 4-tolylthioacetamido, and like substituted phenylthioacetamido groups.

Illustrative of the acylamino groups when $R_4$ is a substituted arylalkyl group of the formula

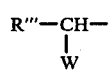

and when W is protected hydroxy are 2-formyloxy-2-phenylacetamido, 2-benzyloxy-2-(4-methoxyphenyl)acetamido, 2-(4-nitrobenzyloxy)-2-(3-chlorophenyl)acetamido, 2-chloroacetoxy-2-(4-methoxyphenyl)acetamido, 2-benzyloxy-2-phenylacetamido, 2-trimethylsilyloxy-2-(4-chlorophenyl)acetamido, 2-benzhydryloxy-2-phenylacetamido and like groups. Representative of such groups when W is protected amino are 2-(4-nitrobenzyloxycarbonylamino)-2-(2-thienyl)acetamido, 2-(2,2,2-trichloroethoxycarbonylamino)-2-phenylacetamido, 2-chloroacetamido-2-(1,4-cyclohexadien-1-yl)acetamido, 2-(4-methoxybenzyloxycarbonylamino)-2-(4-methoxyphenyl)acetamido, 2-benzhydryloxycarbonylamino-2-(3-thienyl)acetamido, 2-(1-carbomethoxy-2-propenyl)amino-2-phenylacetamido, and like groups. Representative of acylamino groups

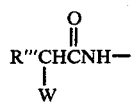

when W is a protected carboxy group are 2-benzyloxycarbonyl-2-phenylacetamido, 2-tert-butoxycarbonyl-2-phenylacetamido, 2-(4-nitrobenzyloxycarbonyl)-2-(2-thienyl)acetamido, 2-benzhydryloxycarbonyl-2-(4-chlorophenyl)acetamido, 2-(4-methoxybenzyloxycarbonyl)-2-phenylacetamido and like groups.

Exemplary of the acylamino group

when $R_4$ is a heteroarylmethyl group of the formula $R''''—CH_2—$ are 2-thienylacetamido, 3-thienylacetamido, 2-furylacetamido, a 2-thiazolylacetamido group of the formula

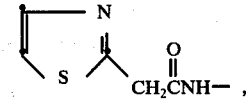

a 1-tetrazolylacetamido group of the formula

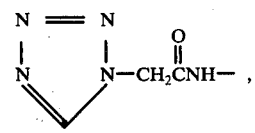

or a 5-tetrazolylacetamido group of the formula

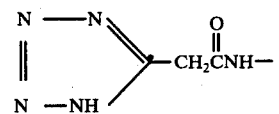

$R_1$ can also be a 3-(2-chlorophenyl)-5-methylisoxazol-4-ylamido group of the formula

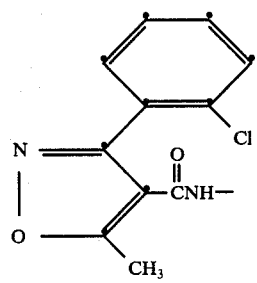

The most preferred side chains for the purpose of this invention are formamido, acetamido, phenylacetamido, phenoxyacetamido, and 2-thienylacetamido. Such side chains are preferred only because 3-halomethylcephem starting materials bearing such side chains have been found to be more readily available.

In general the process of this invention is directed to the preparation of 3-hydroxymethyl-2-cephem compounds from the corresponding 3-halomethylcephems by a 2-step process comprising (1) the nucleophilic displacement of the 3'-halo substituent with an alkali metal salt of a γ- or δ-hydroxycarboxylic acid and (2) the protic acid induced intramolecular lactone formation from the resulting γ- or δ-hydroxy esters with concomitant release of the 3-hydroxymethyl cephem.

In essence the first step of the process is an esterification procedure, that is, an esterification of a γ- or δ- hydroxycarboxylic acid via the reaction of its alkali metal salt with an alkyl halide, here a 3-halomethylcephem. This type of esterification procedure has been described in the chemical literature [J. E. Shaw, D. C. Kunerth, and J. J. Sherry, *Tetrahedron Letters*, 689 (1973)].

As indicated hereinabove both 3-halomethyl-2-cephems and 3-halomethyl-3-cephems can be employed as starting material for the process of the present invention; the reaction of either isomer with the aforedescribed γ- or δ-hydroxycarboxylic acid salts affords, under the conditions of this process, a mixture of the corresponding 2-cephem and 3-cephem γ- or δ-hydroxy esters, which can be separated by chromatography.

The preparation of 3-halomethylcephems, the starting materials for the process of the present invention, has been well documented in the cephalosporin art. Such compounds are available by allylic halogenation of the corresponding desacetoxycephalosporins (U.S. Pat. No. 3,658,799). More recently 3-halomethylcephems have been prepared by cleavage of 3-acetoxymethyl and 3-carbamoyloxymethylcephems with hydrohalic acids [S. Karady, T. Y. Cheng, S. H. Pines and M. Sletzinger, *Tetrahedron Letters*, 30, 2625 (1974)].

Exemplary of 3-halomethylcephems suitable as starting materials for the process of this invention are:
benzhydryl 7-phenylacetamido-3-bromomethyl-3-cephem-4-carboxylate,
4'-nitrobenzyl 7-formamido-3-chloromethyl-2-cephem-4-carboxylate,
2',2',2'-trichloroethyl 7-(2,5-dichlorophenylthioacetamido)-3-iodomethyl-2-cephem-4-carboxylate,
4'-methoxybenzyl 7-(4-nitrobenzyloxycarbonylamino)-3-bromomethyl-3-cephem-4-carboxylate,
tert-butyl 7-[2-(4-nitrobenzyloxycarbonylamino)-2-phenylacetamido]-3-chloromethyl-2-cephem-4-carboxylate,
benzyl 7-(2-thienylacetamido)-3-iodomethyl-2-cephem-4-carboxylate,
trimethylsilyl 7-phenoxyacetamido-3-chloromethyl-3-cephem-4-carboxylate,
4'-nitrobenzyl 7-[2-(4-nitrobenzyloxycarbonyl)-2-phenylacetamido]-3-bromomethyl-2-cephem-4-carboxylate,
benzhydryl 7-benzyloxycarbonylamino-3-chloromethyl-2-cephem-4-carboxylate,
benzhydryl 7-benzamido-2-chloromethyl-2-cephem-4-carboxylate,
4'-methoxybenzyl 7-acetamido-3-bromomethyl-2-cephem-4-carboxylate; and like 3-chloromethyl, 3-bromomethyl and 3-iodomethyl 2- or 3-cephem compounds. The bromomethylcephems are a preferred class of starting materials.

Alkali metal salts which can be employed in the present process include the sodium, potassium and lithium salts of γ- or δ-hydroxycarboxylic acids of the formula

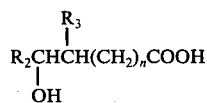

wherein R₂, R₃ and n are as defined hereinabove.

Illustrative of such suitable alkali metal salts are:
sodium 4-hydroxybutanoate,
potassium 4-hydroxybutanoate,
lithium 3-methyl-4-hydroxybutanoate,
lithium 4-hydroxypentanoate,
sodium 3-methyl-4-hydroxypentanoate,
potassium 4-hydroxyhexanoate,
sodium 3-methyl-4-hydroxyhexanoate,
sodium 3-ethyl-4-hydroxyhexanoate,
potassium 3-hydroxymethylpentanoate,
lithium 5-hydroxypentanoate,
sodium 5-hydroxypentanoate,
potassium 4-methyl-5-hydroxypentanoate,
sodium 4-methyl-5-hydroxyhexanoate,
lithium 4-methyl-5-hydroxyheptanoate,
sodium 5-hydroxyhexanoate,
potassium 5-hydroxyheptanoate, and
sodium 4-ethyl-5-hydroxyheptanoate.

Preferred salts are the alkali metal salts of γ-hydroxycarboxylic acids of the formula

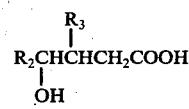

Most preferred are the alkali metal salts of 4(γ)-hydroxybutanoic acid.

Typically the first step of the present process is carried out by adding a suspension of about 1.1 equivalents (per equivalent of 3-halomethylcephem) of the γ- or δ-hydroxycarboxylic acid salt in HMPA to a solution of the 3-halomethylcephem in HMPA at ice bath temperature. The progress of the reaction is followed by comparative thin-layer chromatography, and upon completion of the reaction, typically after about 1 to about 2 hours, the product cephem γ- or δ-hydroxy ester is isolated and purified by conventional laboratory procedures. The intermediate product in the present process, a 2-cephem compound of the formula

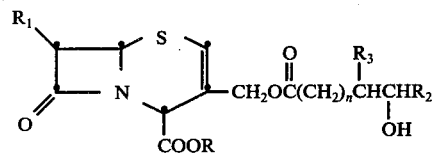

and can be separated from the corresponding 3-cephem compound by column chromatography. Usually, however, the mixture of 2-cephem and 3-cephem hydroxy esters resulting from the first step of the present process is used without separation as starting material for the second step.

Representative of the 2-cephem hydroxy esters, intermediates in the present process and also compounds of the present invention, are
4'-nitrobenzyl 7-acetamido-3-(4-hydroxyhexanoyloxymethyl)-2-cephem-4-carboxylate,
benzhydryl 7-phenylthioacetamido-3-(3-methyl-4-hydroxyhexanoyloxymethyl)-2-cephem-4-carboxylate,
tert-butyl 7-(2-thienylacetamido)-3-(4-hydroxybutanoyloxymethyl)-2-cephem-4-carboxylate,
4'-methoxybenzyl 7-[2-(4-nitrobenzyloxycarbonylamino)-2-phenylacetamido]-3-(4-ethyl-5-hydroxyheptanoyloxymethyl)-2-cephem-4-carboxylate,
2',2',2'-trichloroethyl 7-phenylacetamido-3-(5-hydroxyhexanoyloxymethyl)-2-cephem-4-carboxylate,
benzyl 7-(4-nitrobenzyloxycarbonylamino)-3-(5-hydroxypentanoyloxymethyl)-2-cephem-4-carboxylate, succinimidomethyl 7-(4-methoxybenzyloxycarbonylamino)-3-(3-hydroxymethylpentanoyloxymethyl)-2-cephem-4-carboxylate, benzhydryl 7-phenoxyacetamido-3-(5-hydroxyheptanoyloxymethyl)-2-cephem-4-carboxylate, tert-butyl 7-(2-tert-butoxycarbonyl-2-phenylacetamido)-3-(4-hydroxybutanoyloxymethyl)-2-cephem-4-carboxylate, phenacyl 7-acetamido-3-(3-ethyl-4-hydroxyhexanoyloxymethyl)-2-cephem-4-carboxylate, 4'-chlorophenacyl 7-(4-chlorophenoxyacetamido)-3-(4-hydroxypentanoyloxymethyl)-2-cephem-4-carboxylate, and 4'-nitrobenzyl 7-phenylacetamido-3-(4-hydroxybutanoyloxymethyl)-2-cephem-4-carboxylate.

In the second step of the process of the present invention the intermediate 2-cephem γ- or δ-hydroxy ester is reacted with a protic acid having a pK of less than about 4.0 to promote an intramolecular cyclization of the hydroxy ester moiety. Resultant therefrom is the formation of the 2-hydroxymethyl-2-cephem product of the present process and, as a by-product, a γ- or δ-lactone represented by the formula

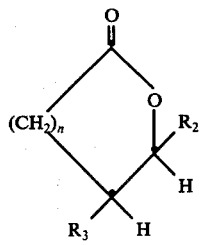

Although the hydroxy ester moiety of the corresponding 3-cephem hydroxy esters undergoes a similar lactonization when reacted with a protic acid having a pK of less than about 4.0, the resulting 3-hydroxymethyl-3-cephem compounds further lactonize under the acidic conditions of the present process to form lactones of the formula

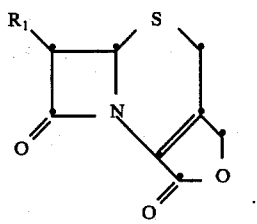

Therefore since the starting material for the second step of the present process is typically a mixture of 2-cephem and 3-cephem hydroxy esters, the product resulting from the acid induced lactonization of step 2 is often a mixture of a 3-hydroxymethyl 2-cephem and the corresponding 3-cephem lactone. The desired 3-hydroxymethyl-2-cephem can be isolated and purified by employing such conventional procedures as fractional crystallization and chromatography.

The particular manner in which the second step of the present process is carried out is not a critical aspect of this invention. It is only necessary that the intermediate cephem hydroxy ester be brought in contact with a protic acid having a pK of less than about 4.0. Any conventional laboratory procedure may be employed to achieve the desired protic acid contact with the substrate cephem hydroxy ester. Most commonly, an acid induced reaction such as the lactonization step of this process is carried out by adding a suitable acid to a solution of the substrate in an inert solvent. Thus, typically, the protic acid induced lactonization of the present process is accomplished by adding the cephem hydroxy ester to a solution of a suitable protic acid in an inert solvent.

Suitable protic acids are those organic and inorganic protic acids having a pK of less than about 4. Exemplary of such are formic acid; haloacetic acids such as chloroacetic acid, dichloroacetic acid, trichloroacetic acid, trifluoroacetic acid and the like; methanesulfonic acid, trifluoromethanesulfonic acid, p-toluenesulfonic acid, and like organic sulfonic acids; and inorganic acids such as chlorosulfonic acid, sulfuric acid, hydrochloric acid and phosphoric acid.

Any of a wide variety of inert organic solvents may be employed as a medium for the lactonization step of the present process. By the term "inert organic solvent" is meant an organic solvent which, under the conditions of the process, does not enter into any appreciable reaction with either the reactants or the products. Suitable solvents include, for example, aromatic hydrocarbons such as benzene, chlorobenzene, toluene, ethylbenzene, xylene and the like; halogenated aliphatic hydrocarbons such as chloroform, methylene chloride, carbon tetrachloride, 1,2-dichloroethane (ethylene chloride), 1,1,2-trichloroethane, 1,1-dibromo-2-chloroethane, and the like; aliphatic nitriles such as acetonitrile or propionitrile; esters such as ethyl acetate, butyl acetate, and the like; ethers such as 1,4-dioxane, tetrahydrofuran, diethyl ether, dimethoxyethane and the like; amides such as N,N-dimethylformamide, N,N-dimethylacetamide or hexamethylphosphoric triamide (HMPA); and like solvents. Halogenated aliphatic hydrocarbons are a preferred class of solvents to be employed in the present process.

It should be noted that the second step of this process can also be carried out by dissolving the substrate cephem hydroxy ester in one of the aforedescribed solvents or a mixture thereof and then mixing or slurrying the resulting solution with an aqueous solution of a suitable acid until the lactonization (3-hydroxymethyl-2-cephem formation) is complete.

The progress of the reaction is followed by comparative thin-layer chromatography. The time required to complete the reaction is dependent on the reaction temperature, the pK of the acid employed, the solvent, and the nature of the particular cephem hydroxy ester substrate. Usually the reaction is complete within about 1 to about 8 hours.

The product 3-hydroxymethyl-2-cephem compounds of the process of this invention are useful as intermediates in the preparation of antibiotics. For example, 3-hydroxymethyl-2-cephems can be converted to the corresponding 7-acylamino-3-carbamoyloxymethyl-3-cephem-4-carboxylic acids in accordance with the process disclosed in U.S. Pat. No. 3,905,963 issued Sept. 16, 1975. Alternatively the 3-hydroxymethyl-2-cephems, prepared in accordance with the present process, can be employed as starting materials in the preparation of 7-acylamino-3-carboxy-3-cephem-4-carboxylic acids of the formula

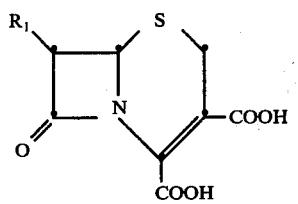

and derivatives thereof as described in U.S. Pat. No. 3,953,436 issuing Apr. 27, 1976.

The following examples are provided to illustrate this invention but are not intended in any way to be limiting on the scope thereof. In the following examples nuclear magnetic resonance spectra were obtained on a Varian Associates T-60 Spectrometer using tetramethylsilane as the reference standard. The chemical shifts are expressed in δ values in parts per million (ppm) and coupling constants (J) are expressed in cycles per second.

EXAMPLE 1

Benzhydryl 7-(2-thienylacetamido)-3-(4-hydroxybutanoyloxymethyl)-2-cephem-4-carboxylate To a solution of 2.24 g. (3.8 mmol) of benzhydryl 7-(2-thienylacetamido)-3-bromomethyl-3-cephem-4-carboxylate in 20 ml. of hexamethylphosphoramide (HMPA) at 0° C. under nitrogen was added a suspension of .530 g. (4.2 mmol) of sodium 4-hydroxybutanoate in 25 ml. of HMPA. After stirring 1.5 hours, ethyl acetate was added, and the resulting solution was washed with water (5X) and brine and dried over anhydrous MgSO$_4$. Evaporation in vacuo to dryness provided 2.12 g. of product which was combined with that of an identical reaction ran on a 1 mmol scale. The combined products were chromatographed on a silica gel column using a cyclohexane:ethyl acetate (1:2) eluant to provide 293 mg. of a mixture of the title product and the corresponding 3-cephem compound. For the title product: nmr (CDCl$_3$) δ1.7–2.6

(m, 4, OCCH$_2$CH$_2$CH$_2$OH), 3.55 (m, 2, CH$_2$OH), 3.83 (s, 2, side chain CH$_2$), 4.63 (bs, 1, —CH$_2$OH), 5.0 (s, 1, C$_4$—H), 5.23 (d, 1, J = 4 Hz, C$_6$—H), 5.58 (dd, 1, J = 4 and 8 Hz, C$_7$—H), 6.42 (bs, 1, C$_2$—H), 6.95 (s, 1, ester CH), and 7.36 (m, 13, thienyl + ArH).

EXAMPLE 2

Benzhydryl 7-(2-thienylacetamido)-3-hydroxymethyl-2-cephem-4-carboxylate.

A. To 100 ml. of a solution of trifluoroacetic acid in methylene chloride (0.297 ml. trifluoroacetic acid in 125 ml. methylene chloride) at 0° C. was added 1.048 g. of a mixture of benzhydryl 7-(2-thienylacetamido)-3-(3-hydroxybutanoyloxymethyl)-2-cephem-4-carboxylate and the corresponding 3-cephem compound. After 6 hours a saturated aqueous sodium bicarbonate solution was added, and the mixture was allowed to warm to room temperature. The organic layer was separated, washed with saturated aqueous sodium chloride solution, dried over anhydrous MgSO$_4$, and evaporated in vacuo to dryness. The foam thereby obtained was dissolved in methylene chloride; 59 mg. of 7-(2-thienylacetamido)-3-hydroxymethyl-3-cephem-4-carboxylic acid lactone (the product derived from the 3-cephem starting material) crystallized and was filtered. The filtrate was concentrated in vacuo and cooled. Another 209 mg. of lactone, mixed with some of the title product, was obtained. Evaporation in vacuo to dryness of the resulting solution provided 680 mg. of the title product: nmr (acetone D-6) δ3.85 (s, 2, side chain CH$_2$), 4.17 (s, 2, —CH$_2$OH), 5.25 (d, 1, J = 4.5 Hz, C$_6$—H), 5.54 (dd, 1, J = 4.5 and 8.0 Hz, C$_7$—H), 6.40 (bs, 1, C$_2$—H), 6.95 (s, 1, ester CH), 7.32 (m, 13, thienyl + ArH), and 8.04 (d, 1, J = 8.0 Hz, side chain NH).

B. To 1 ml. of a solution of formic acid in methylene chloride (0.076 ml. formic acid in 250 ml. of methylene chloride) at room temperature was added 10 mg. of a mixture of benzhydryl 7-(2-thienylacetamido)-3-(3-hydroxybutyroxymethyl)-2-cephem-4-carboxylate and the corresponding 3-cephem compound. The progress of the reaction was followed by comparative tlc. The reaction proceeded more slowly but gave essentially the same results as with trifluoroacetic acid in (A).

I claim:

1. A process for preparing a 3-hydroxymethyl-2-cephem compound of the formula

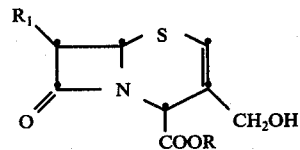

which comprises 1. reacting a 3-halomethylcephem compound of the formula

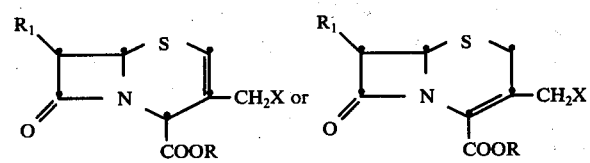

with from about 1 to about 1.3 equivalents of a salt of a γ-hydroxycarboxylic acid of the formula

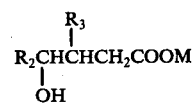

or a salt of a δ-hydroxycarboxylic acid of the formula

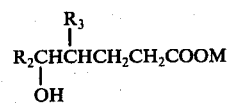

in hexamethylphosphoramide (HMPA) at a temperature of about −10° to about 25° C. to provide a mixture of the 2-cephem hydroxy ester of the formula

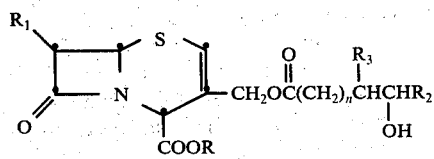

and the corresponding 3-cephem hydroxy ester; and
2. reacting in an inert organic solvent the product 2-cephem hydroxy ester with a protic acid having a pK value of less than about 4.0;

wherein in the above formulae
X is chloro, bromo, or iodo;
M is an alkali metal cation;
n is 1 or 2;
R is a carboxylic acid protecting group;
$R_2$ and $R_3$ are independently hydrogen, ethyl or methyl; and
$R_1$ is an amido group of the formula

wherein $R_4$ is
a. hydrogen, $C_1$-$C_3$ alkyl, 3-(2-chlorophenyl)-5-methylisoxazol-4-yl or 4-protected amino-4-protected carboxybutyl;
b. benzyloxy, 4-nitrobenzyloxy, 2,2,2-trichloroethoxy, tert-butoxy, or 4-methoxybenzyloxy;
c. the group —R" wherein R" is 1,4-cyclohexadienyl, phenyl or phenyl substituted with 1 or 2 substituents independently selected from the group consisting of halo, protected hydroxy, nitro, cyano, trifluoromethyl, $C_1$-$C_3$ alkyl, and $C_1$-$C_7$ alkoxy;
d. an arylalkyl group of the formula

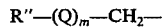

wherein R" is as defined above, Q is O or S, and m is 0 or 1;
e. a substituted arylalkyl group of the formula

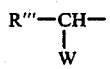

wherein R'" is R" as defined above, 2-thienyl or 3-thienyl, and W is protected hydroxy, protected carboxy or protected amino; or
f. a heteroarylmethyl group of the formula

wherein R'''' is 2-thienyl, 3-thienyl, 2-furyl, 2-thiazolyl, 5-tetrazolyl, and 1-tetrazolyl.

2. The process of claim 1 wherein R is tert-butyl, benzyl, 4-methoxybenzyl, $C_2$-$C_6$ alkanoyloxymethyl, 4-nitrobenzyl, diphenylmethyl (benzhydryl), phenacyl, 4-halophenacyl, 2,2,2-trichloroethyl, succinimidomethyl, and tri($C_1$-$C_3$)alkylsilyl.

3. The process of claim 1 wherein an alkali metal salt of a γ-hydroxycarboxylic acid is employed.

4. The process of claim 3 wherein an alkali metal salt of γ-hydroxybutanoic acid is employed.

5. The process of claim 1 wherein $R_1$ is formamido, acetamido, phenylacetamido, phenoxyacetamido or 2-thienylacetamido.

6. The process of claim 1 wherein the acid employed in the second step is formic acid, chloroacetic acid, dichloroacetic acid, trifluoroacetic acid, trichloroacetic acid, methanesulfonic acid, p-toluenesulfonic acid, trifluoromethanesulfonic acid, chlorosulfonic acid, sulfuric acid, hydrochloric acid or phosphoric acid.

7. The process of claim 1 wherein X is bromo.

8. The process of claim 1 wherein a compound of the formula

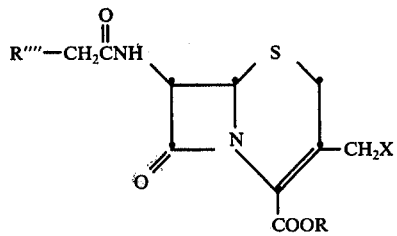

is converted to a compound of the formula

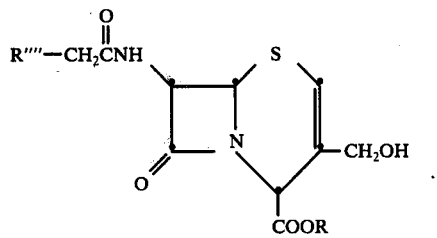

9. The process of claim 8 wherein X is bromo and R'''' is 2-thienyl.

* * * * *